US012685794B2

(12) United States Patent
Allen et al.

(10) Patent No.: US 12,685,794 B2
(45) Date of Patent: Jul. 21, 2026

(54) INTERMITTENT CATHETER STORAGE/STERILISATION

(71) Applicant: ConvaTec Limited, Flintshire (GB)

(72) Inventors: Daniel Allen, Staffordshire (GB); David Pollard, Merseyside (GB)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 19/020,005

(22) Filed: Jan. 14, 2025

(65) Prior Publication Data

US 2025/0152764 A1 May 15, 2025

Related U.S. Application Data

(63) Continuation of application No. PCT/GB2023/051885, filed on Jul. 18, 2023.

(60) Provisional application No. 63/390,350, filed on Jul. 19, 2022.

(30) Foreign Application Priority Data

Aug. 10, 2022 (GB) .................................... 2211714

(51) Int. Cl.
   A61L 2/00    (2006.01)
   A61L 2/20    (2006.01)
   A61L 103/15    (2026.01)
(52) U.S. Cl.
   CPC ............. *A61L 2/20* (2013.01); *A61L 2103/15* (2026.01); *A61L 2202/11* (2013.01); *A61L 2202/122* (2013.01); *A61L 2202/123* (2013.01)

(58) Field of Classification Search
   CPC . A61L 2/202; A61L 2/10; A61L 2/204; A61L 2/18
   USPC ...................................... 422/28, 32, 292, 300
   See application file for complete search history.

(56) References Cited

U.S. PATENT DOCUMENTS

| | | | |
|---|---|---|---|
| 7,334,580 B2 * | 2/2008 | Smaldone | ......... A61M 16/0833 |
| | | | 128/207.14 |
| 10,639,388 B1 * | 5/2020 | Grambergs | ............... A61L 2/10 |
| 2017/0197003 A1 * | 7/2017 | Taggart | ................... A61L 2/202 |
| 2019/0038791 A1 | 2/2019 | Gerrans et al. | |
| 2020/0046865 A1 * | 2/2020 | Shane | ..................... A61L 2/204 |

FOREIGN PATENT DOCUMENTS

| | | |
|---|---|---|
| CN | 210931824 U | 7/2020 |
| CN | 215274744 U | 12/2021 |
| EP | 1380309 A1 | 1/2004 |

(Continued)

OTHER PUBLICATIONS

International Preliminary Report on Patentability for PCT/GB2023/051885; Dated Dec. 18, 2024; 10 Pages.
Search Report for GB2211714.7; dated Jul. 24, 2023; 1 Page.

*Primary Examiner* — Monzer R Chorbaji
(74) *Attorney, Agent, or Firm* — TAFT STETTINIUS HOLLISTER LLP; Ryan O. White; Derek B. Lavender

(57) ABSTRACT

A catheter storage and sterilisation device that has a housing and a removeable cartridge, the cartridge including a catheter-receiving chamber for receiving a catheter. The cartridge being removably attachable to the housing and having an opening in fluid communication with the housing. The housing has a chamber for receiving a sterilisation fluid and a mechanism for supplying a sterilisation fluid to the cartridge via the opening.

16 Claims, 5 Drawing Sheets

(56) References Cited

FOREIGN PATENT DOCUMENTS

| WO | 2020223043 | A1 | | 11/2020 | | |
| WO | 2020252032 | A1 | | 12/2020 | | |
| WO | WO-2020252045 | A1 | * | 12/2020 | ............... | A61L 2/18 |

* cited by examiner (a)

(b)

INTERMITTENT CATHETER STORAGE/STERILISATION

TECHNICAL FIELD OF THE INVENTION

The present invention relates to the storage and/or sterilisation of intermittent catheters (e.g. intermittent urinary catheters).

BACKGROUND TO THE INVENTION

A catheter is a medical device comprising a hollow catheter tube designed for insertion into canals, vessels, passageways or body cavities to permit injection, drainage or withdrawal of fluids or substances therefrom, or to ensure said canals, vessels, passageways etc. remain open. Urinary catheters are designed for use for insertion into a user's bladder via the urethra to drain the bladder.

Catheters, especially intermittent urinary catheters, are typically single-use and are intended to be discarded once used. This can be undesirable as it generates unwanted waste. It is therefore advantageous to provide a re-usable catheter. In order to provide a catheter that is reusable, issues surrounding the storage and sterilisation of the catheter must be addressed.

In an attempt to achieve a means of sterilisation, some prior art solutions provide an outer case into which the catheter can be introduced along with a sterilising solution. Examples of such catheter products are shown in PCT applications No. PCT/US2020/036969 and PCT/US2020/039190. In order to ensure that the entire catheter is sterilised either a sufficient amount of sterilisation solution must be provided to fully immerse the catheter or the case must be agitated (i.e. by the shaking the case). However, such arrangements are not without their drawbacks; where the catheter is fully immersed in sterilising solution a large quantity of sterilising fluid is required and requires the user to recharge it between every use and there is a risk of spillage. When the case is agitated the user may not know when the catheter has been completely treated with the sterilising solution.

Furthermore, to maximise comfort and minimise the risk of trauma and/or infection, an outer surface of the catheter tube is typically wetted using a wetting agent prior to insertion by the user. In further developments, the catheter tube itself comprises, is integrated with or is coated with a hydrophilic component (e.g. a hydrophilic polymer) which serves to reduce friction further upon application of a wetting agent (e.g. water).

Some catheters may be supplied pre-wetted in a packaging, for instance, where the catheter is at least partially submerged within wetting agent within the packaging. Whilst this may ensure the catheter tube is adequately wetted prior to use, such arrangements suffer in that components of the catheter other than the catheter tube such as a gripper element or funnel can also become wetted. This has a detrimental effect of the experience of the user where it may become difficult to hold and direct the catheter tube as required. This is particularly problematic where the user is performing self-catheterisation. Further, having the catheter submerged may effectively reduce the shelf-life of the catheter due to long-term exposure of components of the catheter to moisture.

It is therefore seen advantageous to provide a catheter which may be wetted and/or sterilised at or immediately prior to the point of use.

It is an aim of an embodiment or embodiments of the invention to overcome or at least partially mitigate one or more problems with the prior art and/or to provide an improved intermittent catheter.

SUMMARY OF THE INVENTION

The present invention provides a catheter assembly according to the appended claims.

A broad aspect of the present disclosure provides a catheter storage, sterilisation and/or wetting device: comprising a housing and a removeable cartridge. The cartridge may include a catheter-receiving chamber for receiving a catheter. The cartridge may be removably attachable to the housing. The cartridge may have an opening in fluid communication with the housing. The housing may comprise a chamber for receiving a fluid. The housing may comprise a mechanism for supplying the fluid to the cartridge. The fluid may be supplied via the opening. The fluid may be a sterilisation fluid. The fluid may be a wetting agent. The fluid may be a sterilisation fluid and a wetting agent.

According to a first aspect of the invention there is provided a catheter storage and sterilisation device, the device comprising a housing and a removeable cartridge; the cartridge including a catheter-receiving chamber for receiving a catheter; the cartridge being removably attachable to the housing and having an opening in fluid communication with the housing; the housing comprising a chamber for receiving a sterilisation fluid and a mechanism for supplying the sterilisation fluid to the cartridge via the opening.

The mechanism for supplying the sterilisation fluid may be an atomiser. The mechanism for supplying the sterilisation fluid may be a vaporiser.

The atomiser may be an ultrasonic piezoelectric atomiser. The piezoelectric atomiser may operate at a frequency of between 100 and 200 kHz, preferably, between 140 and 160 kHz, more preferably 142 kHz. The ultrasonic piezoelectric atomiser may be a piezoelectric disc transducer.

Atomisation typically produces a suspension of liquid droplets, with a diameter in the order of 1 µm, in air, referred to as a "mist" or aerosol. The use of ultrasonic atomisation is advantageous as it requires less energy than alternatives such as thermal atomisation and can be electronically controlled. Furthermore, ultrasonic atomisation also atomises any active ingredients held in solution in the sterilisation fluid, allowing a broader range of antimicrobial compounds to be used. It also reduces the amount of sterilisation fluid or liquid required to sterilise the catheter.

The vaporiser may be a thermal vaporiser. The thermal vaporiser may comprise a resistive wire. The resistive wire may be configured to heat the sterilisation to form an aerosol of sterilisation fluid.

Vaporisation provides an alternative means of generating an aerosol of liquid droplets suspended in air.

The sterilisation fluid storage means may comprise a sterilisation fluid storage chamber. The sterilisation fluid storage chamber may be fluidly connected to the catheter-receiving chamber. The sterilisation fluid storage chamber may be transparent or translucent. The sterilisation fluid storage chamber may be subdivided by one or more baffles. The one or more baffles may have a hole therein. The holes may be aligned. Each subdivision may contain sufficient sterilisation fluid for a single sterilisation cycle.

The sterilisation fluid storage chamber may comprise an aperture. The aperture may provide fluid communication between the interior and exterior of the fluid storage chamber. The aperture may be in fluid communication with, optionally aligned with, the holes in the one or more baffles. The aperture may be sealed with a cap prior to use. The cap may be removeable by the user prior to use. The aperture may be sealed with foil. The foil may be pierced by the catheter storage and sterilisation device during insertion.

The fluid storage chamber may comprise a fluid absorbing material. The fluid absorbing material may be arranged in each sub-division. The fluid absorbing material may extend through the holes in the baffles. The fluid absorbing material may extend to the aperture in the sterilisation fluid storage chamber. The fluid absorbing material may be a foam. The fluid absorbing material may be fibrous. The fluid absorbing material may provide a wicking action.

By providing a wicking material in the sterilisation fluid storage chamber, the risk of spillage of sterilisation fluid is reduced. Furthermore, the orientation of the operation of the device becomes less dependent upon the orientation of the device which is beneficial in a portable, handheld, device.

The sterilisation fluid storage means may be integrally formed in the device. The sterilisation fluid storage means may be removeable from the device.

The sterilisation fluid storage means may further comprise a port to refill the sterilisation liquid. The port may comprise a one-way valve. The sterilisation fluid storage means may be refilled via a syringe.

The sterilising solution may be hypochlorous acid solution. The sterilisation fluid may be selected from one of the following: chlorine dioxide, sodium hypochlorite, sodium hydroxide, sodium chloride, chlorine, hydrogen peroxide, photosensitisers, chloroazodin, dichlordimethylhydantoin, permanganate, alcohols (e.g. ethanol and/or isopropanol), phenols (e.g. phenol, thymol and/or chloroxyphenol), aldehydes (e.g. glutaraldehyde and/or noxythiolin) and/or acids (e.g. acetic acid, citric acid, peracetic acid and/or diperoxy dodecanoic acid) or combinations thereof. For example, the sterilisation solution may comprise sodium hypochlorite with sodium chloride; or the sterilisation solution may comprise sodium hypochlorite with sodium hydroxide; or the sterilisation solution may comprise sodium hypochlorite with hypochlorous acid; or the sterilisation solution may comprise chlorine with hypochlorous acid.

The catheter-receiving chamber may be elongate. The catheter receiving chamber may be tubular. The catheter-receiving chamber may be formed from a transparent material. The catheter-receiving chamber may have an interior wall. The catheter-receiving chamber may have an exterior wall. The exterior wall of the catheter-receiving chamber may form the exterior wall of the catheter storage and sterilisation device. The exterior wall of the catheter-receiving chamber may comprise an exterior wall of an external housing. The catheter-receiving chamber may be formed from a translucent material. The catheter-receiving chamber may be formed of plastic. A first end of the catheter-receiving chamber may comprise an opening to allow insertion of the catheter. A second end of the catheter-receiving chamber may be in fluid communication with the sterilisation fluid storage means. The fluid communication between the catheter-receiving chamber and the sterilisation fluid storage means may be via the atomiser.

The catheter storage and sterilisation device may further comprise a catheter. The catheter may be a urinary catheter. The catheter may be an intermittent urinary catheter. The sterilisation (preferably the atomiser or vaporiser) device may be arranged proximate to an insertion end of the catheter.

The catheter-receiving chamber may comprise a catheter holder. The catheter holder may not engage with the catheter tube. The catheter holder may comprise one or more ribs, projections, pips, pins fins or the like. The catheter holder may comprise one or more ribs. The catheter holder may engage with the catheter funnel. The catheter holder may engage with the catheter connector. The catheter holder may retain the catheter centrally within the catheter-receiving chamber. The ribs may project radially inwards from the inner wall of the catheter-receiving chamber. The ribs may be configured to engage with the catheter at a connector arranged thereon. The catheter may further comprise a funnel. The catheter may further comprise a catheter tube. The connected may be arranged between the funnel and the catheter tube. The funnel and connector may be integrally formed. The funnel may comprise a textured exterior surface. The exterior surface may provide a handling surface. Advantageously, where the catheter holder attaches to the catheter at a point other than the catheter tube this ensures that the entire surface of the catheter tube can be sterilised.

The catheter-receiving chamber may be integrally formed with a sterilisation unit. The catheter-receiving chamber may be provided with a cap. The catheter-receiving chamber and cap may be attached with a snap fit, for example an annular snap fit. The catheter-receiving chamber and cap may be attached with a fixed fit. The catheter-receiving chamber and cap may be attached with a snap fit. The catheter-receiving chamber and cap may be attached with a screw fit. A seal may be provided between the catheter-receiving chamber and cap. The seal may be an O-ring. The seal may be an X-ring. The seal may be a U-cup seal. The catheter-receiving chamber may be configured such that upon removal of the cap, a handling surface on the catheter is exposed.

The cartridge may be formed of translucent material. The cartridge may comprise a catheter-receiving chamber. The housing may comprise a sterilisation unit.

The cartridge and housing may be attached with a fixed fit. The cartridge and housing may be attached with a snap fit, for example an annular snap fit. The cartridge and housing may be attached with a screw fit. A seal may be provided between the cartridge and housing. The seal may be an O-ring. The seal may be an X-ring. The seal may be a U-cup seal.

The catheter-receiving chamber may be attached to the sterilisation unit by means of a fixed fit. The catheter-receiving chamber may be attached to the sterilisation unit by means of a snap fit, for example an annular snap fit. The catheter-receiving chamber may be attached to the sterilisation unit by means of a screw fit. A seal may be provided between the catheter-receiving chamber and the sterilisation unit. The seal may be an O-ring, an X-ring or a U-cup seal. The catheter-receiving chamber may be configured such that upon being detached from the sterilisation unit, a handling surface on the catheter is exposed.

Advantageously, the provision of a seal improves the time that the catheter-receiving chamber remains sterile after sterilisation. This means that in some instances the catheter may be sterilised some time prior to use, for example, when initially inserted, allowing the catheter to be deployed quicker (i.e. without running a sterilisation cycle immediately before use). For example, immediately after using a catheter, it may be inserted into the device and sterilised; it may then remain sealed in the device for several hours, potentially even overnight, until the user next needs to drain their bladder.

The catheter-receiving chamber may further comprise a UV LED. The catheter-receiving chamber may comprise a plurality of UV LEDs. The one or more LEDs may have a wavelength of between 200 and 300 nm.

Advantageously, the provision of a UV LED provides a secondary means of sterilising the catheter.

The catheter-receiving chamber may further comprise a catheter warming means. The catheter warming means may be a heater. The catheter warming means may be a heating element. The heating element may be a resistive wire heater. The resistive wire may be provided on a wall of the catheter-receiving chamber, for example on the interior wall of the catheter-receiving chamber. The resistive wire may be arranged around the catheter-receiving chamber. The resistive wire may be coiled around the interior wall of the catheter-receiving chamber. The resistive wire may be wound helically around the interior wall. The resistive wire may be arranged radially outward of the catheter. The catheter warming means may be chemically activated. For example, the catheter warming means may comprise a chemical mixture, which is activable to create an exothermic reaction. Various approaches are known for this, as are well known in the field of disposable hand warmers. For example, the chemical mixture may be air-activated (based on iron or a nanoparticle composite of zinc and carbon) or may use a supersaturated solution (such as sodium acetate solution).

The catheter storage device may be configured to sterilise the catheter prior to warming. The sterilisation and warming may be initiated simultaneously. By providing a means of warming the catheter prior to use the user experience is improved as a source of discomfort is reduced.

The catheter-receiving chamber may further comprise a sensor. The sensor may be configured to detect the presence of a catheter within the catheter-receiving chamber. The sensor may be a proximity sensor. The sensor may be an ultrasonic proximity detector. The sensor may be an optical sensor. The catheter storage and sterilisation device may be configured to be activated in response to a signal from the sensor. The atomiser or vaporiser may be configured to be activated when the catheter is inserted into the catheter-receiving chamber. The sensor may be configured to detect when the catheter is inserted into the catheter-receiving chamber. The sensor may be configured to activate the atomiser or vaporiser. The sensor may be configured to detect when the catheter is inserted into the catheter-receiving chamber and in response to activate the atomiser or vaporiser.

The catheter-storage and sterilisation device may further comprise a switch. The atomiser or vaporiser may be configured to be activated by the switch. The switch may be configured to only be activatable a predetermined number of times. The switch may be a push button. The predetermined number of activations may be controlled by a PCB controller. The switch may comprise a mechanical latching wheel. The mechanical latching wheel may determine the predetermined number of activations. The switch may be resettable (i.e. the counter for the number of times the device has been activated may be reset to zero). The predetermined number of activations may be at least 2, 3, 4, 5, 6, 7, 8, 9 or 10. The predetermined number of activations may be no more than 20, 19, 18, 17, 16, 15, 14, 13, 12, 11, 10, 9, 8, 7, 6 or 5. For example, the predetermined number of activations may be between 5 and 10, for example 7. This would accord with approximately the number of times a catheter might need to be used (and hence sterilised) over the course of a single day.

Although the sterilisation allows the catheter to be used more than once, catheters may still have a finite lifespan. By including a means of monitoring this and/or limiting the number of activations, the ease of use for the user is improved and chance of over-use is therefore reduced. By providing a means of resetting the counter, the catheter storage and sterilisation device can be used over the lifespan of multiple catheters, thereby reducing waste.

The catheter-storage and sterilisation device may further comprise one or more indicators. The or an indicator, for example a first indicator may indicate that the device is operational, for example that the device is sterilising. The or an indicator, for example a second indicator may indicate that the device has completed the sterilisation. The indicators may be LEDs. The indicator may be an LCD display. Where the device has a predetermined number of activations, the LCD display may indicate the status thereof.

The catheter storage and sterilisation device may further comprise a sterilising unit. The sterilising unit may comprise an electronics package. The electronics package may comprise a PCB controller. The PCB controller may comprise a timer. The PCB controller may comprise a counter. The PCB controller may be operably connected to the atomiser or vaporiser. The PCB controller may be operably connected to the UV LED. The PCB controller may be operably connected to the catheter warming means. The atomiser or vaporiser, and catheter warming means may be initiated by a single activation of the switch. The PCB controller may be operably connected to the sensor. The PCB controller may comprise a Bluetooth module. The timer may be configured to deactivate the atomiser or vaporiser after a predetermined time. The timer may be configured to deactivate the catheter warming means after a predetermined time.

The electronics package may comprise a battery. The battery may be rechargeable. The battery may be recharged via a USB connection.

By providing the device with a battery the portability of the device is improved. A user can wet or sterilise the catheter at a convenient time and place.

The catheter storage and sterilisation device may further comprise a sterilisation unit. The sterilisation unit may comprise one or more of the following: the sterilisation fluid storage means, the atomiser, the vaporiser, the battery, the PCB controller, the or more indicators. An external wall of the sterilisation unit may comprise an external wall of an external housing of the device.

The catheter storage and sterilisation device may comprise a plurality of catheter-receiving chambers. Each catheter-receiving chamber may be in fluid communication with a separate sterilisation fluid storage chamber. Fluid communication with the separate sterilisation fluid storage chamber may be via separate atomisers or vaporisers. The plurality of catheter-receiving chambers may alternatively be in fluid communication with a single sterilisation fluid storage chamber. The plurality of catheter-receiving chambers may be in fluid communication with a single sterilisation fluid storage chamber via a single atomiser or vaporiser. Alternatively, each of the plurality of catheter-receiving chambers may be associated with a separate atomiser or vaporiser, each atomiser or vaporiser in fluid communication with a single sterilisation fluid storage chamber.

The catheter storage and sterilisation device may comprise an external housing. The catheter may be a female intermittent catheter. The catheter may have a length of between 90 mm to 200 mm. The catheter may have a length of between 100 mm and 150 mm or for example between 130 mm and 155 mm, such as about 135 mm.

The external housing may have an elongate shape. The external housing may have a tubular shape. The external housing may have a length of between 150 mm to 300 mm.

The catheter-receiving chamber may define a portion of the external housing. The sterilisation unit may define a portion of the external housing.

The external housing may be manufactured, imported and sold independently of the catheter. The catheter assembly may comprise a catheter.

The main body and/or cap may be rigid. The rigidity of the main body and cap may be configured to be resiliently deformable to aid a fixed fit of the cap on the main body.

The external housing may be comprised of plastic. The external housing may be comprised of thermoplastic. The cap and main body may be comprised of different materials. The external housing (optionally the cap or main body) may be comprised of polycarbonate; the external housing (optionally the cap or main body) may be comprised of polyethylene; the external housing (optionally the cap or main body) may be comprised of nylon.

The catheter comprises a catheter tube and an outlet body. The catheter may comprise an insertion end for inserting into the urethra and an outlet end from which fluid is drained during use. The outlet end may comprise one or more flow enhancing features such as a funnel which diverges along the flow direction. The outlet end may comprise an external handling surface. The external handling surface may be exposed for a user to handle when a cap is removed. The external handling surface may be exposer for a user to handle when the catheter-receiving chamber is removed. The external handling surface may comprise one or more surface features to enhance a user's grip. The one or more surface features may comprise one or more grooves. The catheter tube may comprise one or more inlets for receiving urine at an insertion end thereof.

The catheter tube may be functionalised. For example, it may comprise, be integrated with or be coated with a hydrophilic component (e.g. a hydrophilic polymer). The hydrophilic component serves to reduce friction further upon application of the wetting agent. At least an external surface of the catheter tube may be functionalised, e.g. the hydrophilic component may be provided on at least an external surface of the catheter tube (which is in contact with the urethra in use). The catheter may comprise a main flow path for the passage of urine. The main flow path may extend along and define a longitudinal axis of the catheter. The main flow path may be provided by a wall of catheter tube. The main flow path may have a proximal inlet at an insertion end of the catheter, and a distal outlet.

The catheter may comprise an outlet body. The outlet body may incorporate the terminal end of the catheter tube. The outlet body may comprise the external handling surface of the catheter. The outlet body may comprise one or more flow enhancing features for aiding the flow from catheter tube. The one or more flow enhancing features may comprise a funnel, for example.

The outlet body may comprise or be referred to as a connector which connects the outlet end, e.g. a funnel and/or the external handling features, and the catheter tube.

Optional features set out above may apply to any aspect of the invention described below. Thus, for example, the type of atomiser and sterilisation fluid are only described once above, but apply to all aspects and combinations of aspects and other optional features. Equally optional features set out below may apply to the above aspect of the invention or any further aspects disclosed below.

According to a second aspect of the invention there is provided a method assembling a catheter storage and sterilisation device comprising a cartridge, a housing and a catheter, wherein the housing comprises a chamber for receiving a sterilisation fluid and a mechanism for supplying the sterilisation fluid to the cartridge; the method comprising; inserting the catheter into the cartridge and then attaching the cartridge to the housing.

The catheter storage and sterilisation device may be the catheter storage and sterilisation device according to the first aspect of the invention, which may optionally include any of the optional features set out above.

The method may further comprise removing the catheter from the catheter-receiving chamber after sterilising the catheter. The catheter may be removed by the user handling a catheter handling means on the catheter.

The method may further comprise introducing the sterilised catheter into a urethra.

According to a third aspect of the invention there is provided a catheter storage device comprising a catheter-receiving chamber for receiving a catheter and a catheter warming means, the catheter warming means configured to warm the catheter.

Advantageously, by providing a means of warming the catheter prior to use the user experience is improved as a source of discomfort is reduced.

According to a fourth aspect of the invention there is provided a method of warming a catheter; the method comprising inserting a catheter into a catheter storage device, activating a catheter warming means, and warming the catheter.

The catheter storage device may be a catheter storage and sterilisation device. The catheter storage and sterilisation device may be the catheter storage and sterilisation device according to the first aspect of the invention and the catheter storage device may optionally include any optional features outlined above.

The catheter storage device may further comprise a sterilisation device. The method may further comprise sterilising the catheter. The sterilisation of the catheter may be performed prior to the step of warming the catheter.

The method may further comprise removing the catheter from the catheter-receiving chamber after warming the catheter. The catheter may be removed by the user handling a catheter handling means on the catheter.

The method may further comprise introducing the warmed catheter into a urethra.

According to a fifth aspect of the invention there is provided a catheter storage and sterilisation device comprising a catheter-receiving chamber for receiving a catheter, a sterilisation mechanism and a sensor, wherein the sensor is configured to activate the sterilisation mechanism in response to detecting the introduction of a catheter into the catheter-receiving chamber.

According to a sixth aspect of the invention there is provided a method activating a sterilisation mechanism; the method comprising providing a catheter storage and sterilisation device comprising a sensor and sterilisation mechanism, and a catheter; inserting the into the catheter storage and sterilisation device, the sensor detecting the presence of the catheter, in response the sensor activating the sterilisation mechanism, and the catheter being sterilised.

The sterilisation means may be an atomiser. The sterilisation means may be a vaporiser.

The catheter storage and sterilisation device may be the catheter storage and sterilisation device according to the first aspect of the invention and the catheter storage and sterilisation device may optionally include any optional features outlined above.

The method may further comprise removing the catheter from the catheter-receiving chamber after sterilising the catheter. The catheter may be removed by the user handling a catheter handling means on the catheter.

The method may further comprise introducing the sterilised catheter into a urethra.

A broad aspect of the present disclosure provides a catheter storage, sterilisation and/or wetting device comprising: a catheter-receiving chamber and an atomiser or vaporiser. The device may further comprise a liquid storage means. The liquid storage means may contain liquid. The atomiser may be configured to atomise the liquid to form an atomised fluid. The vaporiser may be configured to vaporise the liquid to form a vapourised fluid. The atomised fluid may be supplied to the catheter-receiving chamber. The vapourised fluid may be supplied to the catheter-receiving chamber. The liquid may be a sterilising fluid.

According to a seventh aspect of the invention there is provided a catheter storage and sterilisation device; the device comprising a catheter-receiving chamber for receiving the catheter; a sterilisation fluid storage means for storing sterilisation fluid and an atomiser or vaporiser configured to atomise or vaporise the sterilisation fluid to form an atomised or vaporised sterilisation fluid and to supply the atomised or vapourised sterilisation fluid to the catheter-receiving chamber.

According to another broad aspect of the invention there is provided a method of wetting (e.g.) sterilising a catheter, the method comprising; inserting a catheter into a catheter storage, sterilisation or wetting device, activating an atomiser or a vaporiser, atomising or vaporising a fluid (for example a sterilisation fluid), and directing the atomised or vaporised fluid onto the catheter to wet the catheter. The fluid could be a lubrication fluid, such as water to activate a hydrophilic surface of a catheter.

According to an eighth aspect of the invention there is provided a method of sterilising a catheter, the method comprising; inserting a catheter into a catheter storage and sterilisation device, activating an atomiser or a vaporiser, atomising or vaporising a sterilisation fluid, and directing the atomised or vaporised sterilisation fluid onto the catheter to sterilise the catheter.

The catheter storage and sterilisation device may be the catheter storage and sterilisation device according to the first aspect of the invention. The housing may be a sterilisation unit according to the first aspect of the invention. The mechanism may be the atomiser according to the first aspect of the invention. The mechanism may be the vaporiser according to the first aspect of the invention. Of course, the catheter storage and sterilisation device may optionally include any optional features outlined above.

The method may further comprise the step of activating the mechanism. The method may further comprise the step of detaching the cartridge from the housing. The method may further comprise the step of removing the sterilised catheter from the cartridge. The method may further comprise introducing the sterilised catheter into a urethra.

According to a ninth aspect of the invention there is provided a kit of parts including a catheter sterilisation device; the device comprising; a sterilisation fluid storage means for storing sterilisation fluid and an atomiser or vaporiser configured to atomise or vaporise the sterilisation fluid to form an atomised or vaporised sterilisation fluid, the kit further comprising at least one cartridge and at least on catheter.

The kit may comprise a plurality of cartridges, for example, two cartridges, or three cartridges. The kit may comprise a plurality of catheters, for example 5, 10, 20, 30 catheters. The kit may comprise a plurality of cartridges and a plurality of catheters. The kit may comprise more catheters than cartridges.

By providing a kit comprising a plurality of cartridges, the useable life of the kit can be extended, with the cartridges replaced as needed.

DETAILED DESCRIPTION OF THE INVENTION

In order that the invention may be more clearly understood one or more embodiments thereof will now be described, by way of example only, with reference to the accompanying drawings, of which:

The one or more embodiments are described above by way of example only. Many variations are possible without departing from the scope of protection afforded by the appended claims.

Figure 1:
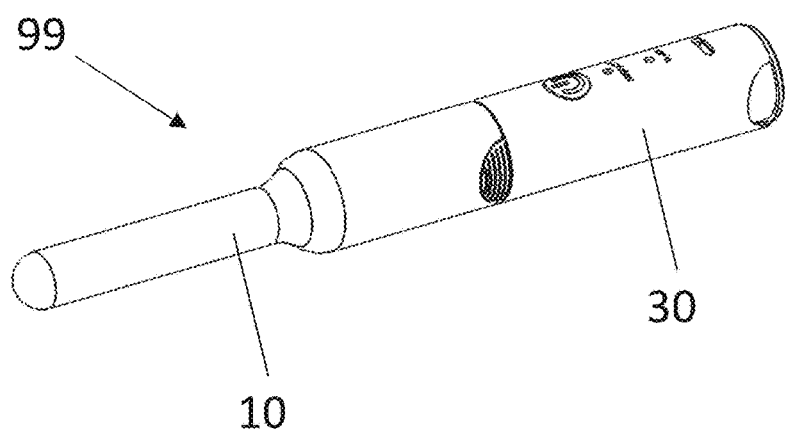
FIG. 1 shows a perspective view of a catheter storage and sterilisation device according to an embodiment of the disclosure.

FIG. 1 shows a perspective view of a catheter storage and sterilisation device 99 according to a first embodiment of the present invention. The catheter storage and sterilisation device 99 comprises a cartridge 10 and a sterilisation unit 30.

Figure 2:
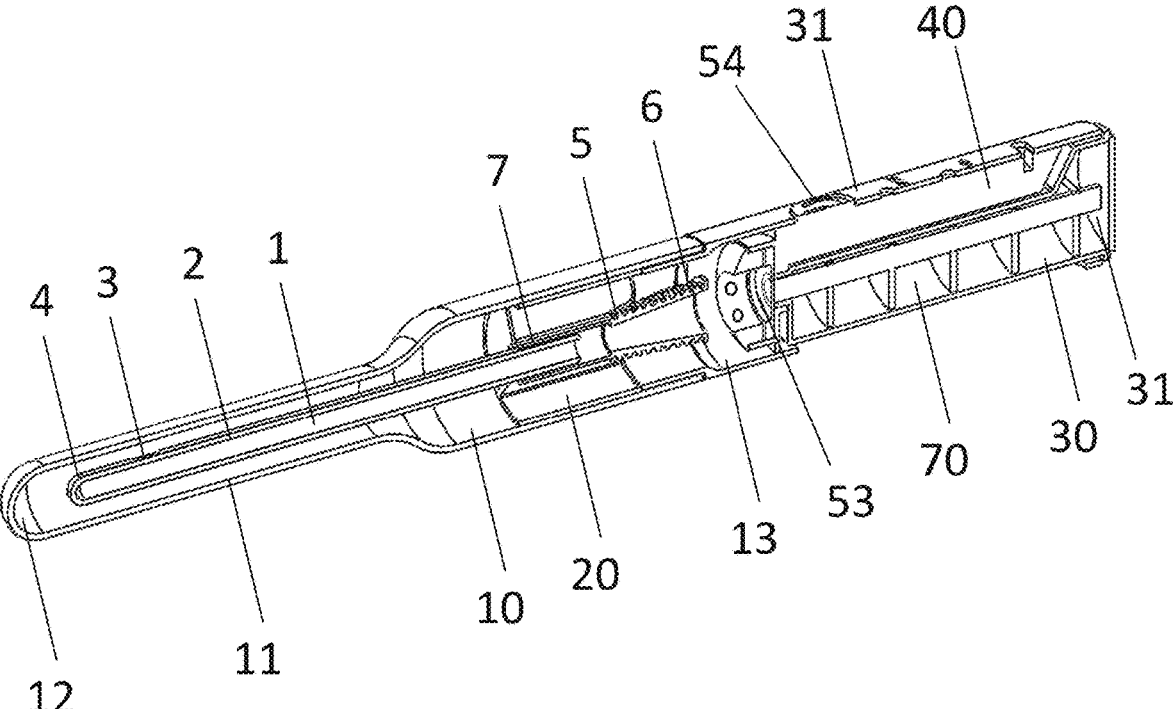
FIG. 2 shows a cross sectional schematic view of the catheter storage and sterilisation device of FIG. 1.

FIG. 2 shows a cross sectional view of the catheter storage and sterilisation device 99. The cartridge or catheter-receiving chamber 10 of this embodiment is defined by the interior of an elongate plastic tube 11 with a closed, distal, end 12 and an open, proximal end 13. Arranged within the catheter-receiving chamber 10 is a catheter holder 20. Also shown is a catheter 1, the catheter 1 comprising a catheter tube 2 with a hole 3 arranged near the distal, insertion, end 4 and a funnel 5 arranged at the proximal, drain, end 6. The funnel 5 is attached to the catheter tube 2 via a connector 7.

Arranged at the proximal end 13 of the catheter-receiving chamber 10, the sterilisation unit 30 of this exemplary embodiment comprises a tubular steriliser body 31 with an open, distal, end 32 and an opposing proximal end 33. Within the steriliser body 31 there is provided an electronics package 40, a sterilisation fluid storage chamber 70 and a piezoelectric atomiser 53. Arranged on the outer surface of the steriliser body is a switch 54 operably connected to the electronics package 40 to control the sterilisation unit 30.

Figure 3:
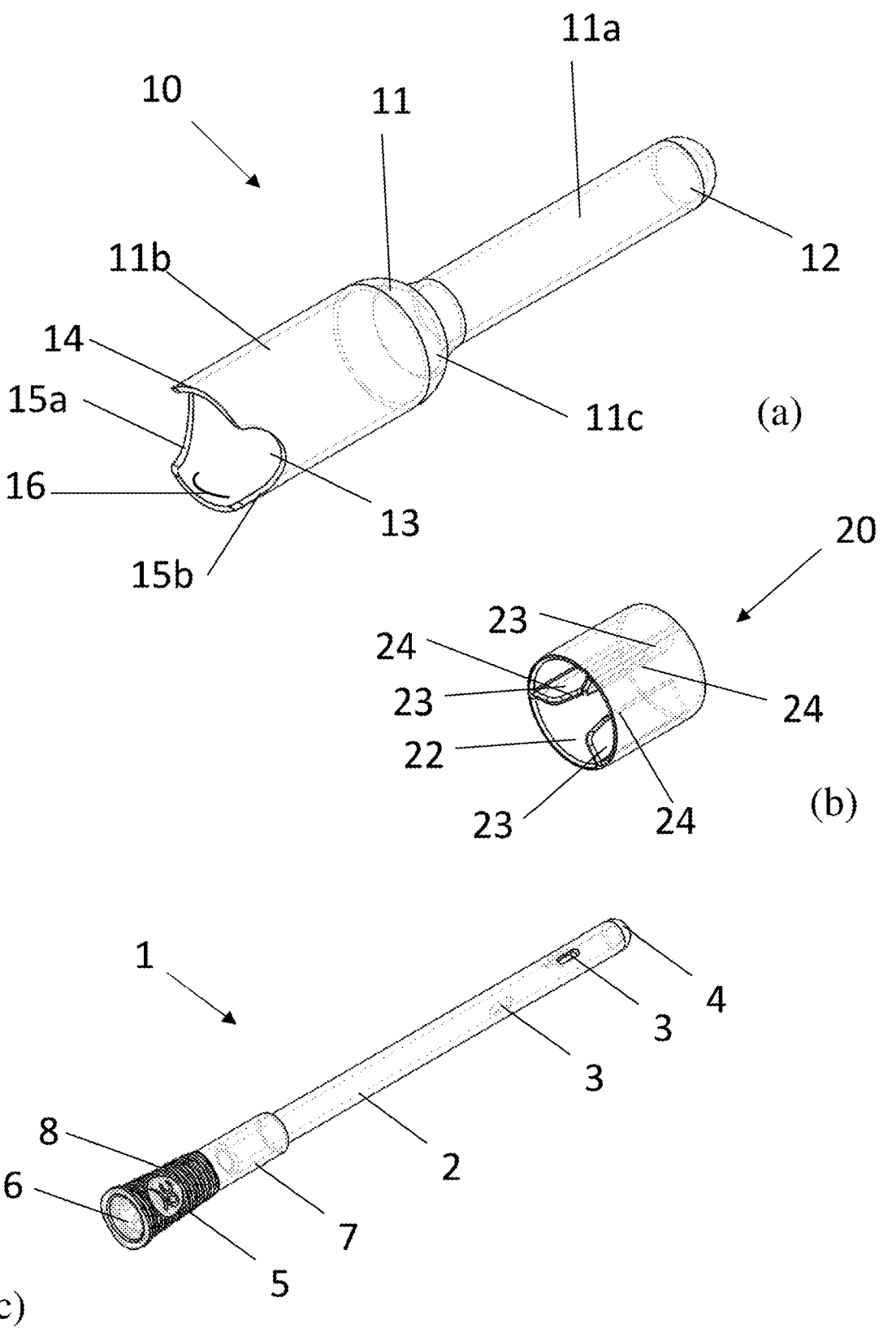
FIG. 3 shows an exploded perspective view of the catheter-receiving chamber of the device of FIG. 1.

With reference to FIG. 3 the cartridge of this embodiment is shown in greater detail, with the catheter-receiving chamber 10, catheter holder 20 and catheter 1 shown separately. The tube 11 which forms the body of the chamber 10 is formed with two diameters, a first section 11a proximate to the closed, distal, end 12 and a wider second section 11b proximate to the open, proximal end 13, the two sections 11a,b are of approximately equal length and joined by a tapered section 11c. The edge 14 of the open proximal end 13 includes two semi-circular portions 15a,b removed to allow fitting to the sterilization unit 30 as described in more detail below. On the inner surface of the chamber 10 arranged close to the end is an engaging projection 16 which engages with a corresponding feature on the sterilising unit 30 which will be described in detail below, this provides a snap fit. The cartridge 10 is formed by moulding from a translucent material.

FIG. 3b shows the catheter holder 20 of this embodiment which comprises a short section of tubular plastic 21 with an outer diameter corresponding to the inner diameter of the second section 11b of the cartridge 10. On the interior surface 22 of the catheter holder 20 are provided three ribs 23 arranged equidistantly around the circumference, the ribs 23 extend parallel to the rotational axis of the catheter holder and project radially inwards. The radially inward facing edges of the ribs 23 define engaging surfaces 24 which engage with the catheter 1, as such a circle defined by the engaging surfaces is approximately equal to the outer diameter of the connector 7 (described below).

FIG. 3c shows the catheter 1, in this instance a female urinary catheter. The catheter comprises an elongate tubular portion 2, the catheter tube 2 is closed at the distal, insertion, end 4 with a hemispherical cap. Proximate to the distal end 4 there is provided two holes 3 which allow fluid communication between the outside of the catheter tube 2 and the hollow interior. The funnel 5 is provided at the proximal, drain, end 6 of the catheter tube, the funnel 5 is attached to the catheter tube 2 via a connector 7, the connector 7 is integrally formed with the funnel 5. The funnel and connector are hollow, and the interior surface of the connector connects to the exterior surface of the catheter tube via a fixed fit. The funnel 5 has an open end in fluid communication with the opening 3 via the interior of the catheter tube to allow fluid to drain during use. The funnel 5 also has a textured outer surface such that it can provide grip to a user when used as a handling means 8. The outer surface of the catheter tube 2 may be functionalised, for example it may be made from or coated in a water activated lubricant and/or antimicrobial material.

Whilst the embodiment is directed at a female intermittent urinary catheter, with an exemplary length of between 90 mm to 200 mm e.g. between 130 mm and 155 mm, such as about 135 mm, it is considered that teachings could be applied to male urinary intermittent catheters (which are typically longer) or even other types of catheters.

Figure 4:
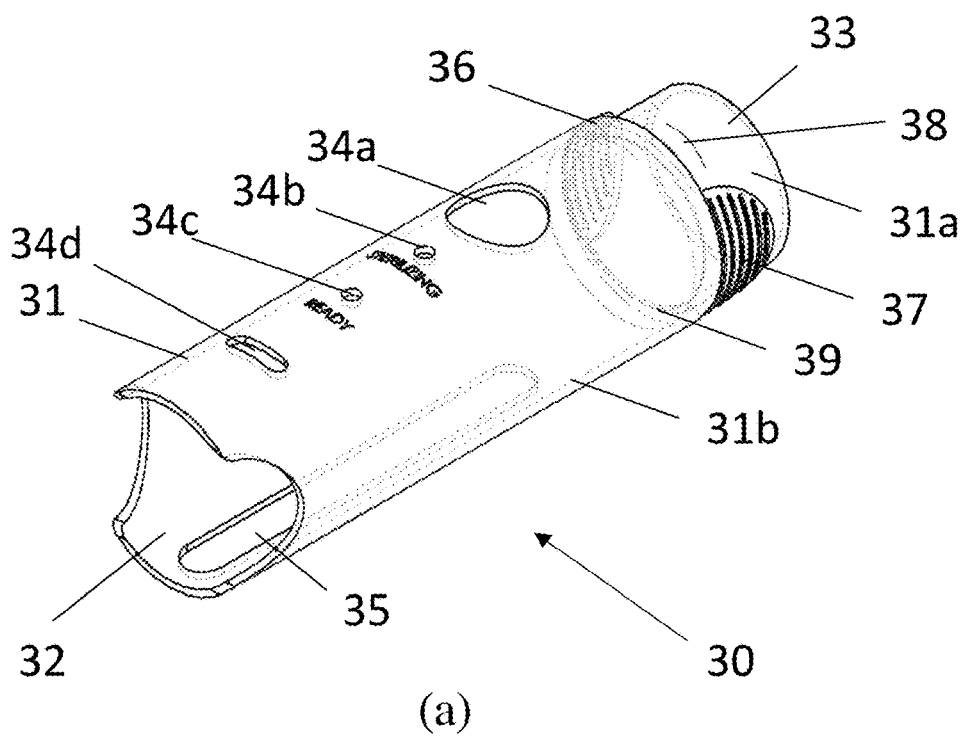
FIG. 4 shows a schematic view of the sterilisation unit of the catheter storage and sterilisation device of FIG. 1.
Figure 4:
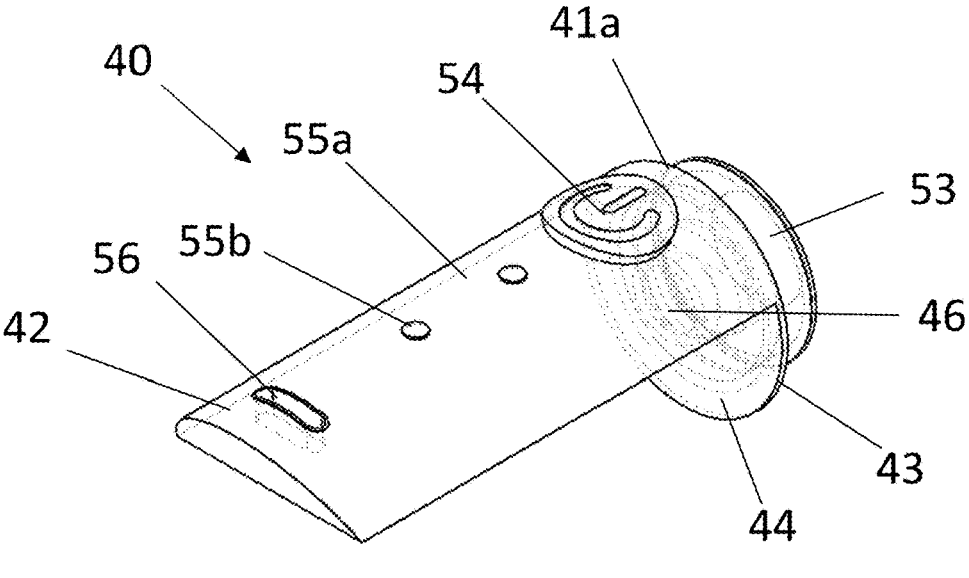

With reference to FIGS. 4a-b the sterilisation unit 30 of this exemplary embodiment is shown in greater detail. The steriliser body 31 is formed of a translucent plastic and is hollow with two open ends 32,33. Proximate to the proximal end 33 there is a step 36 in the steriliser body 31 to form an attaching surface 31a where the outer diameter is reduced such that it is equal to the inner diameter of the second portion 11b of the cartridge 10. Provided on opposing sides of the step are two semi-circular textured gripping features 37 which correspond to the semi-circular portions 14a,b in the cartridge 10. Between these two gripping features 37 and on opposing sides of the step are two recesses 38 (of which one is shown), which engage with the corresponding projections 16 on the cartridge 10.

The main section 31b of the steriliser body 31 has an outer diameter equal to the outer diameter of the second portion 11b of the cartridge 10, such that when joined (as described below) they form a flush unit.

The main section 31b of the steriliser body 31 is provided with four holes 34 through the body 31 and arranged parallel to the longitudinal axis of the body 31, the four holes include a first hole 34a for the switch 54, a second hole 34b and a third hole 34c for indicia, and a fourth hole 34d for a USB charger port, the details of which will be expanded upon below. Opposite the four holes 34 there is provided a slot 35 though the steriliser body 31 from the exterior to the interior, the slot 35 extends parallel to the longitudinal axis of the body 31.

On the interior surface of the steriliser body 31 radially inwards of the step 36 is provided an annular projection 39 projecting radially inwards, the annular projection provides a stop 39 for the electronics package 40 and sterilisation fluid storage chamber 70 as will be explained in greater detail below.

Figure 5:
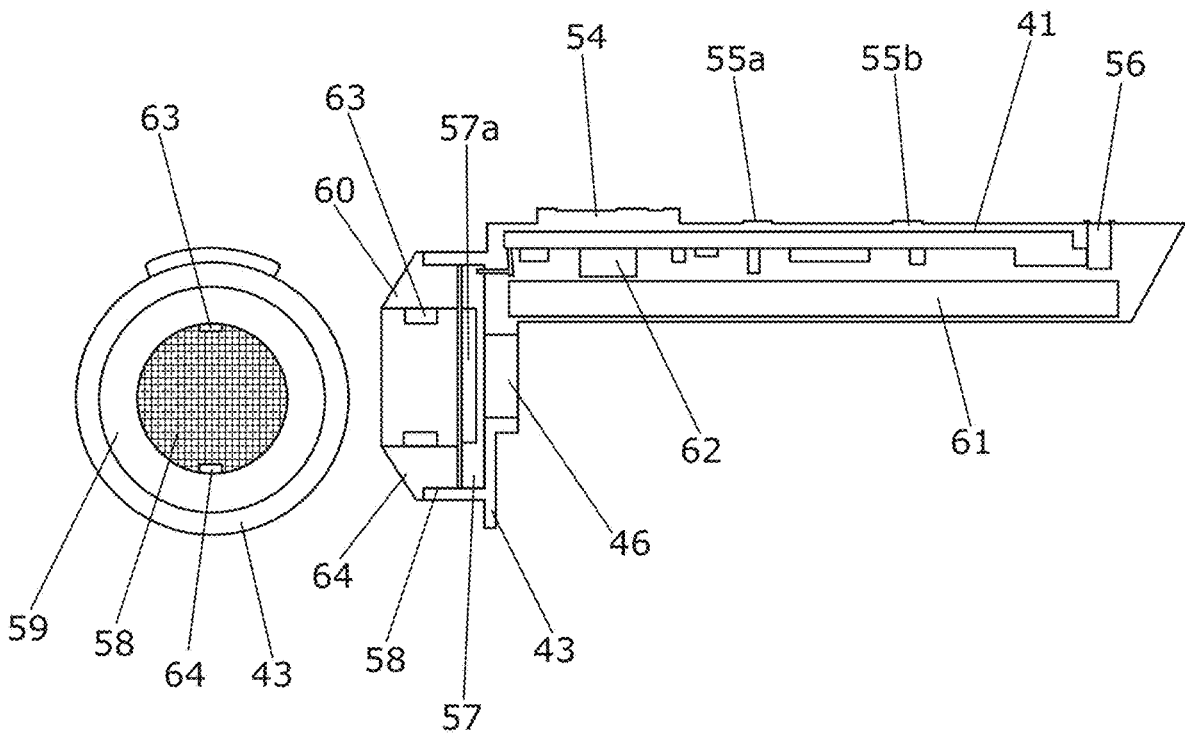
FIG. 5 shows a cross-sectional schematic view of the electronic components of the catheter storage and sterilisation device of FIG. 1.

With reference to FIGS. 4b and 5 the exemplary electronics package 40 is described in greater detail. The electronics body 41 has an overall prism shape with an arc cross section such that the curved surface 42 has a radius equal to the radius of the inner face of the main section 31b of the steriliser body 31. One end 41a of the electronics body 41 is provided which a disk-shaped extension 43 arranged perpendicular to the long axis of the electronics body 41 such that the planar face 44 of the extension is normal to the electronics body 41, the disk 43 is sized to complete the partial circle of the arc of the electronics body 41. A circular aperture 46 is provided in the centre of the disk 43.

The piezo-electric atomiser 53 is provided on the face of the disk 43 facing away from the electronics body 41. The piezo-electric atomiser comprises an annular ceramic piezo-electric element 57 with an aperture 57a therein, the aperture is covered by a stainless-steel mesh 58 attached to the face of the annular ceramic piezo-electric element. Arranged on the opposite side of the stainless-steel mesh 58 is a droplet guide flange 59, the droplet guide flange 59 is a tubular component, the longitudinal axis of which is normal to the plane of the stainless-steel mesh 58. The end of the droplet guide flange 59 distal from the mesh 58 is tapered on its radially outer edge, the tapered edge 60 aids with assembly as will be outlined below. The disk 43, disk aperture 46, piezo-electric atomiser aperture 57a, stainless-steel mesh 58 and droplet guide flange 59 are all co-axially arranged. In some embodiments the piezo-electric atomiser may be replaced with a thermal vaporiser. The thermal vaporiser comprises a coil of thin wire (i.e. sufficiently thin that it heats up to the vaporisation temperature of the sterilisation fluid, arranged between the catheter-receiving chamber and the sterilisation fluid storage chamber.

In some embodiments, on the inner wall of the droplet guide flange 59 is provided a UV LED 63. The wavelength of the LED is selected such that it has antimicrobial properties, for example it has a wavelength of 200 nm to 300 nm.

In some embodiments the inner wall of the droplet guide flange 59 is provided with a sensor 64, such as an ultrasonic proximity sensor configured to detect the presence of the catheter 1 in the catheter receiving chamber 10. In other embodiments alternative sensors are used such as optical sensors.

The electronics body 41 contains the electronic components of the device, on the curved surface 42 is mounted the switch 54, two indicator lights 55a,b and a USB C charger port 56. Internally the body comprises a battery 61 and a PCB controller 62. In some embodiments recharging the battery 61 may be done via wireless charging, in such embodiments the USB C charger port 56 may be omitted.

During assembly the electronics package 40 is inserted into the steriliser body 31 via the opening at the distal end 32 of the steriliser body 31. The electronics package 40 is inserted with its droplet guide flange 59 first, with the tapered edge 60 helping to guide the electronics package 40 into the steriliser body 31. The electronics package 40 is inserted until the disk 43 abuts the stop 39 on the interior of the steriliser body 31, the electronics package 40 and steriliser body 31 are rotationally aligned such that the switch 54, indicator lights 55*a,b* and USB charger port 56 align with the corresponding holes 34*a,b,c* in the steriliser body 31.

Figure 6:
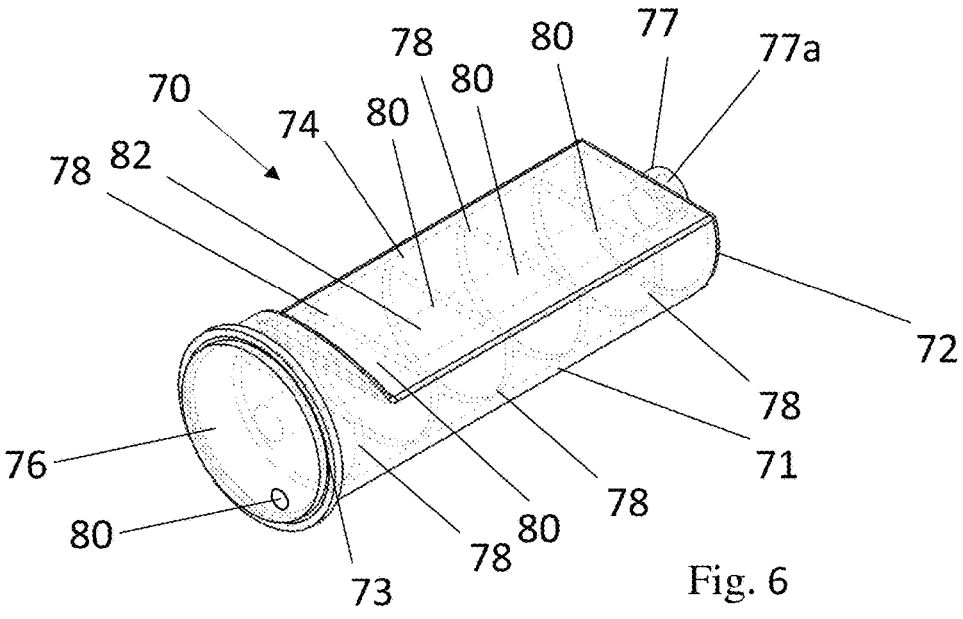
FIG. 6 shows a perspective schematic view of the sterilisation fluid storage chamber of the catheter storage and sterilisation device of FIG. 1.

With reference to FIG. 6, the sterilisation fluid storage chamber 70 of this particular embodiment is described in detail. The sterilisation fluid storage chamber is defined by an enclosure 71 formed by a tubular body with a closed proximal end 72 and an open distal end 73 and is formed of a semi-translucent plastic. An arc section conforming in size to the electronics body 41, extending from the proximal end is removed thereby providing the enclosure with a flat face 74, the flat face 74 does not extend the entire length of the enclosure thus at the distal end 73 of the enclosure the enclosure has a circular cross-section.

A collar 75 is provided projecting radially outwards proximate to the distal end 73 of the enclosure. The distal end 73 is closed by an end cap 76, provided as a separate component for ease of assembly and press fit into place. In some embodiments the centre of the distal end 73 there may be provided a loading/reloading port 80 which extends into the interior of the enclosure and is sealed with a one-way valve. Where a loading/reloading port is provided the sterilisation fluid storage chamber may be formed as part of the sterilisation unit 30 and thus not be removeable.

The proximal end 72 of the enclosure is provided with a tip 77, the tip 77 is a tubular protrusion extending along the longitudinal axis of the enclosure away from the enclosure and arranged co-axially with the enclosure. The tip 77 comprises an aperture 77*a* providing fluid communication with the interior of the enclosure 71.

The interior of the sterilisation fluid storage chamber 70 is provided with baffles, and in this embodiment there are five baffles 78 arranged normal to the longitudinal axis of the chamber 70, the baffles 78 separating the chamber 70 into six separate sections. Fluid communication between the separate sections is provided by a hole 80 in each baffle 78, each hole 80 is aligned with the aperture 77*a* in the tip 77. A cylindrical fibre reed 82 is inserted through these holes extending through along the longitudinal length of the chamber and to the aperture 77*a* of the tip 77. In some embodiments the baffles may be omitted. In further embodiments the sterilisation fluid storage chamber 70 may be provided with an absorbent foam filling in place of the fibre reed and, optionally, the baffles. Those skilled in the art will appreciate that various arrangements of the interior of the sterilisation fluid storage chamber 70 can be provided so long as sterilisation fluid is provided in fluid communication with the atomiser/vaporiser.

The sterilisation fluid storage chamber 70 may be filled with a sterilisation fluid prior to sealing of the end cap 76, or, when present, via the reloading/reloading port 80, the exemplary sterilisation fluid in this embodiment is a hypochlorous acid solution. In other embodiments alternative sterilisation fluids may be selected, for example from the following: chlorine dioxide, sodium hypochlorite, sodium hydroxide, sodium chloride, chlorine, hydrogen peroxide, photosensitisers, chloroazodin, dichlordimethylhydantoin, permanganate, alcohols (e.g. ethanol and/or isopropanol), phenols (e.g. phenol, thymol and/or chloroxyphenol), aldehydes (e.g. glutaraldehyde and/or noxythiolin) and/or acids (e.g. acetic acid, citric acid, peracetic acid and/or diperoxy dodecanoic acid) or combinations thereof.

Figure 7:
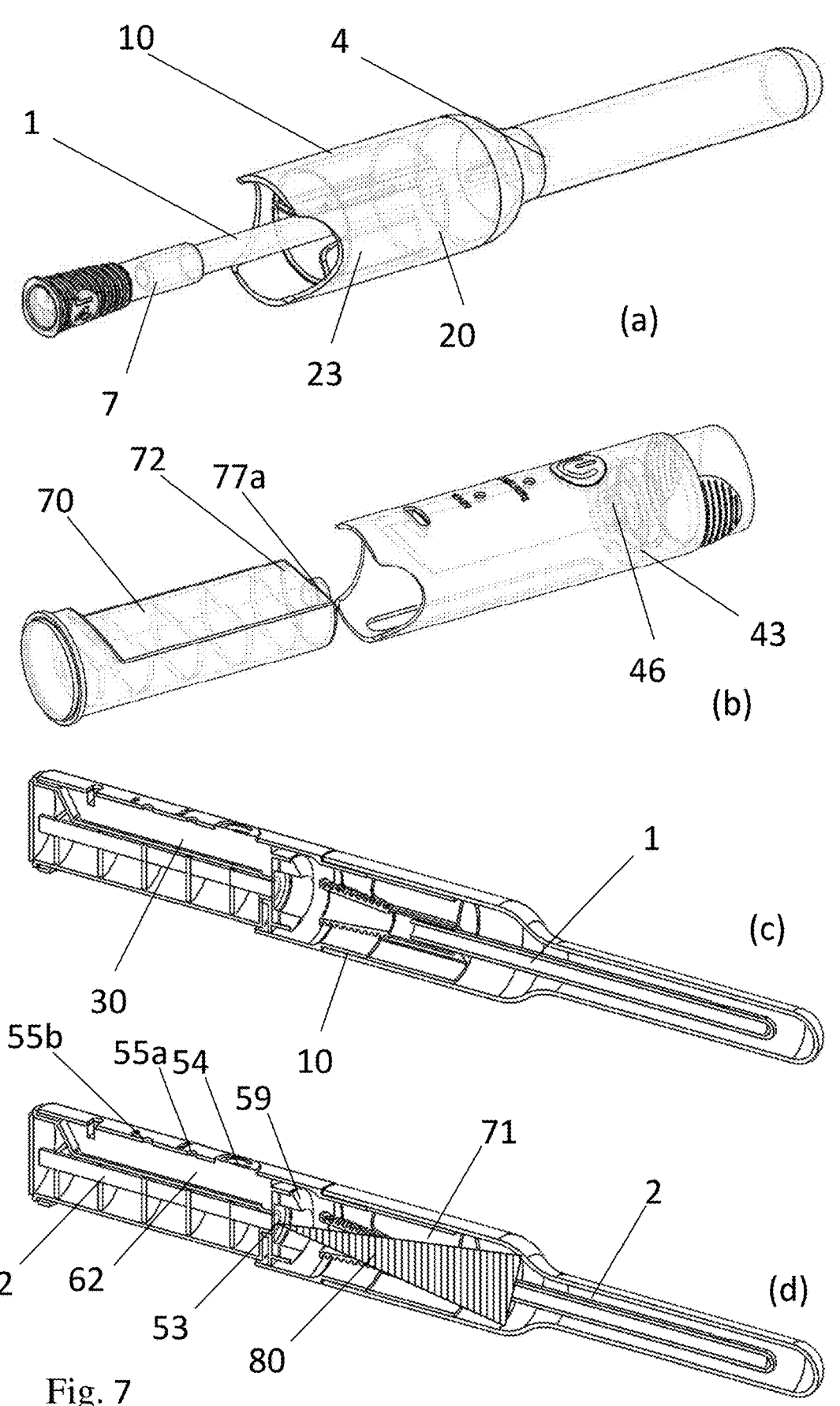
FIG. 7 shows a perspective view of the assembly and use of the device of FIG. 1.

With reference to FIG. 7 the operation of catheter sterilisation and storage device 99 is described.

After the catheter 1 has been used it is rinsed by the user it is inserted distal end 4 first into the catheter-receiving chamber 10 the ribs 23 guiding it in as shown in FIG. 7*a*. The ribs 23 limit the extent to which the catheter 1 can be inserted into the catheter-receiving chamber 10, align it centrally within the chamber 10 and retain it in place. When fully inserted into the catheter-receiving chamber 10, the connector 7 is in contact with the ribs 23 such that the entire surface of the catheter tube 2 can be coated by the sterilisation fluid.

Next the sterilisation fluid storage chamber 70 is inserted into the sterilisation unit 30 as shown in FIG. 7*b*. First a protective cap may be removed from the tip 77, to allow the sterilisation fluid to exit the chamber 70, in alternative embodiments the aperture 77*a* may be sealed with a foil seal that is punctured by the sterilisation unit 30 upon insertion or removed by the user. The sterilisation fluid storage chamber 70 is inserted proximal end 72 first, with the tip entering the disk aperture 46, the chamber 60 is inserted until the proximal end 72 abuts the disk 43. The sterilisation fluid storage chamber 70 is retained in the sterilisation unit with and fixed fit. It is not always necessary to insert the sterilisation fluid storage chamber 70 prior to using the catheter steriliser, in some embodiments the sterilisation fluid storage chamber 70 may contain sufficient sterilisation fluid for multiple sterilisation cycles. In such instances the user proceeds onto attaching the catheter-receiving chamber 30 to the sterilisation unit 30 as outlined below. Where the sterilisation fluid storage chamber 70 contains fluid for multiple sterilisation cycles the slot 35 can be used to observe the fluid in the sterilisation fluid storage chamber 70 to ensure there is sufficient.

Next the catheter-receiving chamber 10 is attached to the steriliser unit 30 as shown in FIG. 7*c*. The attaching surface 31*a* is inserted into the open, proximal end 13 of the catheter-receiving chamber 10 until the step 36 abuts the edge 15 of the proximal end 13, wherein the corresponding engaging projection 16 and recess 38 thereby sealing the catheter 1 in the catheter-receiving chamber 10. In some embodiments this seal is further provided by an O-ring arranged on the attaching surface 31*a* or the interior of the catheter-receiving chamber 10. The catheter sterilisation and storage device 99 is now fully assembled.

Just prior to use of the catheter 1, the user presses the switch 54, the PCB controller 62 then directs an electric current to the piezo-electric atomiser 53 from the battery and activates the first indicator light 55*a* which indicates that the device is sterilising. The piezo-electric atomiser 53 of this particular embodiment oscillates at a frequency (e.g. of 142 kHz) which causes the sterilising fluid in the fibre reed 82 to be atomised emitting a mist 80 of sterilising fluid. The mist 80 is propelled away from the atomiser 53 and is directed by the guide flange 59 towards the catheter 1. The mist 80 fills the interior of the catheter-receiving chamber 71 and sterilising fluid is deposited on all exposed surfaces, including the catheter tube 2. In other embodiments the PCB controller 62 activates the piezo-electric atomiser 53 in response to a signal received from the sensor 64 upon detection of the catheter 1.

To ensure that the catheter 1 is sufficiently sterilised the PCB controller 62 may include a timer unit, this ensure that the sterilising fluid mist 80 is maintained for sufficient duration. During this time the first indicator light 55*a* is illuminated, indicating that sterilisation is occurring, once the sterilisation is complete, the first indicator light 55*a* is switched off and the second indicator light 55*b* is illuminated, indicating that sterilisation is complete, and that the user can remove the catheter 1 for use.

Once the sterilisation process is complete, the user can remove the catheter 1 for use by separating the cartridge 10 and the sterilisation unit 30, then using the handling surfaces 8 on the funnel 5 the catheter 1 can be removed from the cartridge. By using the handling surfaces 8, the user ensures that the now sterile catheter tube 2 is not contaminated prior to use.

During use the cartridge 10 is subjected to the sterilisation fluid and UV light, this may damage the cartridge 10 over time. Therefore, in some embodiments, the cartridge may be disposed of periodically, for example daily, every two days, or weekly. The sterilisation unit 30 containing the more expensive components can then be used for a longer period without needing to be replaced.

The invention claimed is:

1. A catheter storage and sterilisation device; the device comprising a housing and a removeable cartridge;

the cartridge including a catheter-receiving chamber therein for receiving a catheter;

the cartridge being removably attachable to the housing and having an opening in fluid communication with the housing;

the housing comprising a chamber for receiving a sterilisation fluid and a mechanism for supplying a sterilisation fluid to the cartridge via the opening; and a tubular catheter holder arranged within the catheter-receiving chamber comprising a plurality of ribs projecting radially inward from an interior surface thereof and a radially inward facing the plurality of ribs defining an engaging surface configured to engage with the catheter, wherein the cartridge is formed of a translucent material, and wherein the tubular catheter holder comprises an outer diameter corresponding to an inner diameter of the catheter receiving chamber.

2. The catheter storage and sterilisation device according to claim 1, wherein the ribs are configured to engage with the catheter at a connecter arranged thereon.

3. The catheter storage and sterilisation device according to claim 2, wherein the catheter further comprises a catheter tube and a funnel, and wherein the connector is arranged between the catheter tube and funnel.

4. The catheter storage and sterilisation device according to claim 3, wherein the funnel comprises a textured exterior surface which provides a handling surface.

5. The catheter storage and sterilisation device according to claim 1, wherein the mechanism for supplying a sterilisation fluid is an atomiser.

6. The catheter storage and sterilisation device according to claim 5 wherein the atomiser is a piezo-electric atomiser.

7. The catheter storage and sterilisation device according to claim 1 wherein the cartridge and housing are attached with an interference fit.

8. The catheter storage and sterilisation device according to claim 1 wherein the cartridge and housing are attached with an annular snap fit.

9. The catheter storage and sterilisation device according to claim 1 wherein there is provided a seal between the cartridge and housing.

10. The catheter storage and sterilisation device according to claim 1 further comprising a urinary catheter.

11. The catheter storage and sterilisation device according to claim 10 wherein the catheter is an intermittent catheter.

12. The catheter storage and sterilisation device according to claim 10 wherein an atomiser is arranged proximate to an insertion end of the catheter.

13. The catheter storage and sterilisation device according to claim 1 further comprising an external housing, the external housing having an elongate shape.

14. The catheter storage and sterilisation device according to claim 1 wherein an exterior wall of the catheter-receiving chamber comprises an exterior wall of an external housing of the device.

15. The catheter storage and sterilisation device according to claim 1 further comprising a sterilisation unit comprising one or more of the following: the sterilisation fluid storage means, the atomiser, the vaporiser, a battery, a PCB controller, one or more indicators.

16. The catheter storage and sterilisation device according to claim 15 wherein an external wall of the sterilisation unit comprises an external wall of an external housing of the device.

\* \* \* \* \*